US00PP22040P3

(12) United States Plant Patent
Stewart et al.

(10) Patent No.: US PP22,040 P3
(45) Date of Patent: Jul. 26, 2011

(54) STRAWBERRY PLANT NAMED 'DRISSTRAWFOURTEEN'

(50) Latin Name: *Fragaria×ananassa*
Varietal Denomination: DrisStrawFourteen

(75) Inventors: Philip J. Stewart, Watsonville, CA (US); Martin P. Madesko, Watsonville, CA (US); JoAnne F. Coss, Watsonville, CA (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/590,071

(22) Filed: Nov. 2, 2009

(65) Prior Publication Data

US 2011/0107482 P1 May 5, 2011

(51) Int. Cl.
*A01H 5/00* (2006.01)

(52) U.S. Cl. ..... Plt./209

(58) Field of Classification Search ..... Plt./208, Plt./209

See application file for complete search history.

*Primary Examiner* — Susan B McCormick Ewoldt
(74) *Attorney, Agent, or Firm* — Jondle & Associates, P.C.

(57) ABSTRACT

This invention relates to a new and distinct cultivar of strawberry plant named 'DrisStrawFourteen'. The new cultivar is primarily characterized by a medium density plant with medium vigor, medium-sized fruit having a large hollow center, and a partially everbearing habit, is disclosed.

3 Drawing Sheets

Genus and species: *Fragaria×ananassa*.
Variety denomination: 'DrisStrawFourteen'.

BACKGROUND OF THE NEW PLANT

The present invention relates to a new and distinct strawberry cultivar designated 'DrisStrawFourteen' and botanically known as *Fragaria×ananassa*. This new strawberry cultivar was discovered in Monterey County, Calif. in May 2005 and originated from a cross between the proprietary female parent '159K312' (unpatented) and the proprietary male parent '128K296' (unpatented). The original seedling of the new cultivar was first asexually propagated by stolons or tissue culture at a nursery in Shasta County, Calif.

'DrisStrawFourteen' was subsequently asexually propagated in Shasta County, Calif. and underwent further testing in Monterey County, Calif. for five years. The present invention has been found to retain its distinctive characteristics through successive asexual propagations via stolons and tissue culture.

DESCRIPTION OF THE PHOTOGRAPHS

The accompanying color photographs show typical specimens of the new cultivar at various stages of development as nearly true as it is possible to make in color reproductions. The photographs were taken from 9-month-old plants.

DESCRIPTION OF THE NEW CULTIVAR

Figure 1:
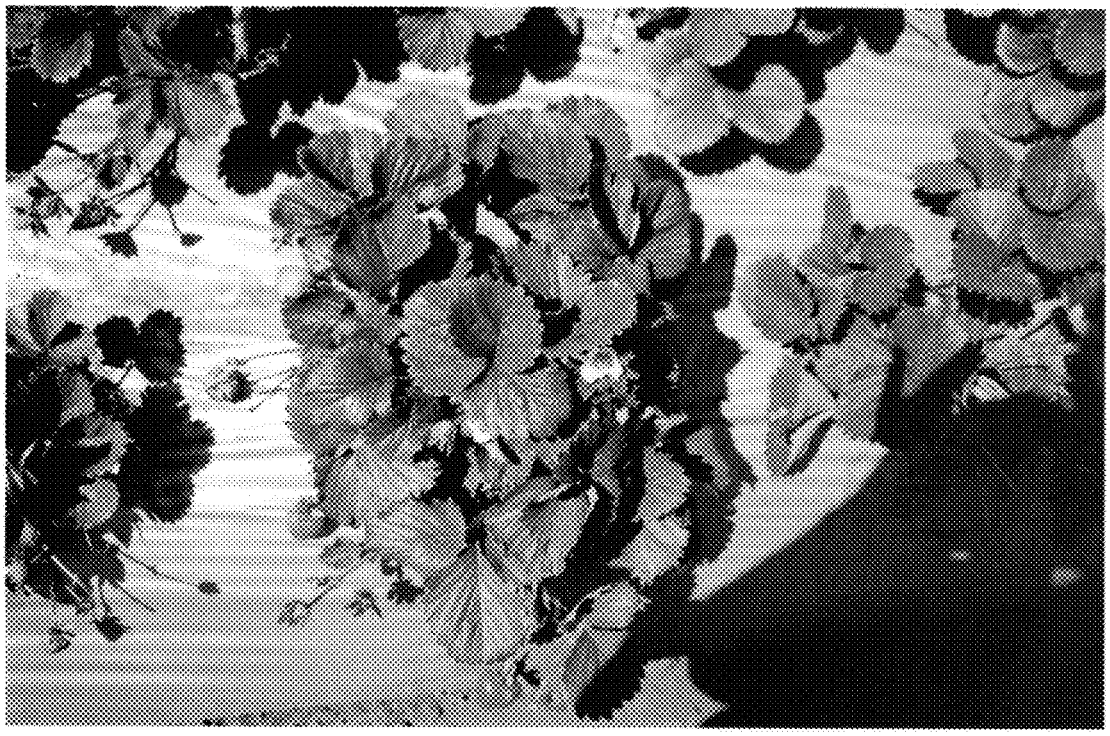
FIG. 1 shows overall plant habit including fruit at various stages of development.
Figure 2:
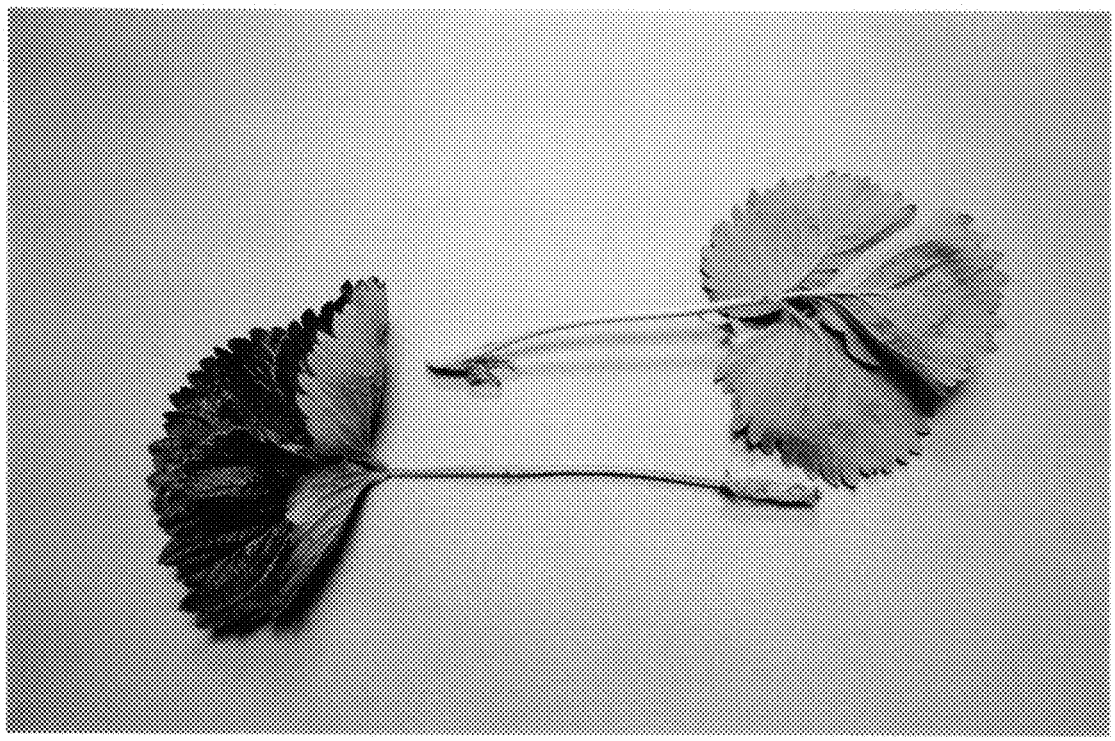
FIG. 2 shows leaves of the plant with three leaflets.
Figure 3:
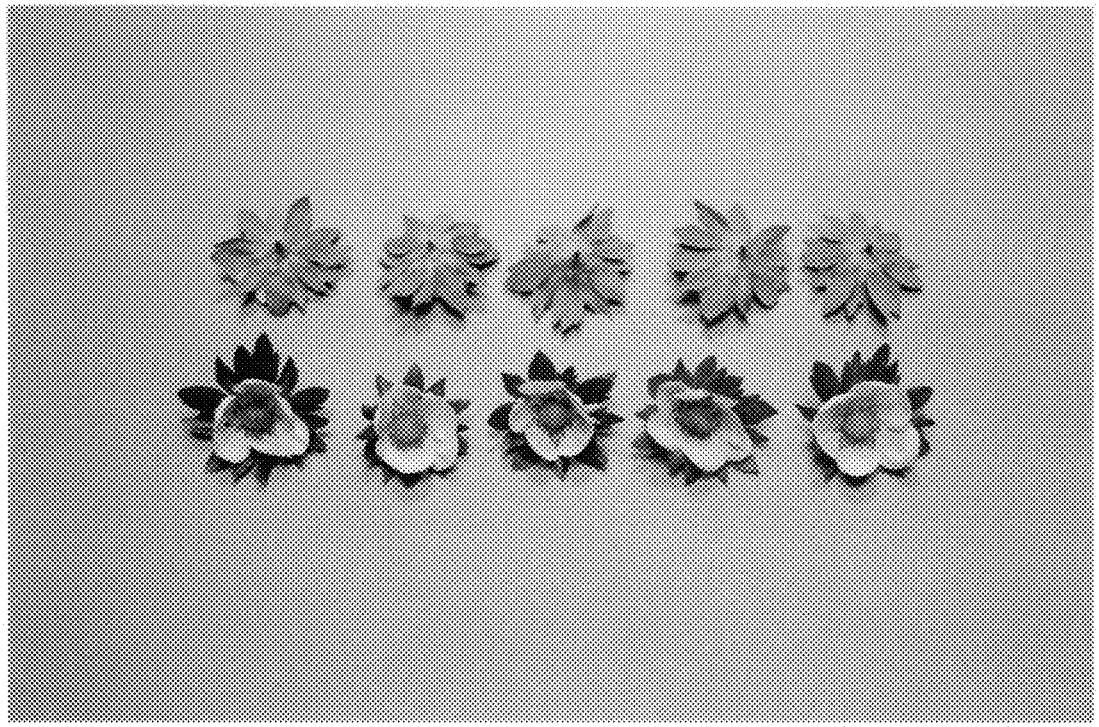
FIG. 3 shows both the upper side and underside of several of the flowers.
Figure 4:
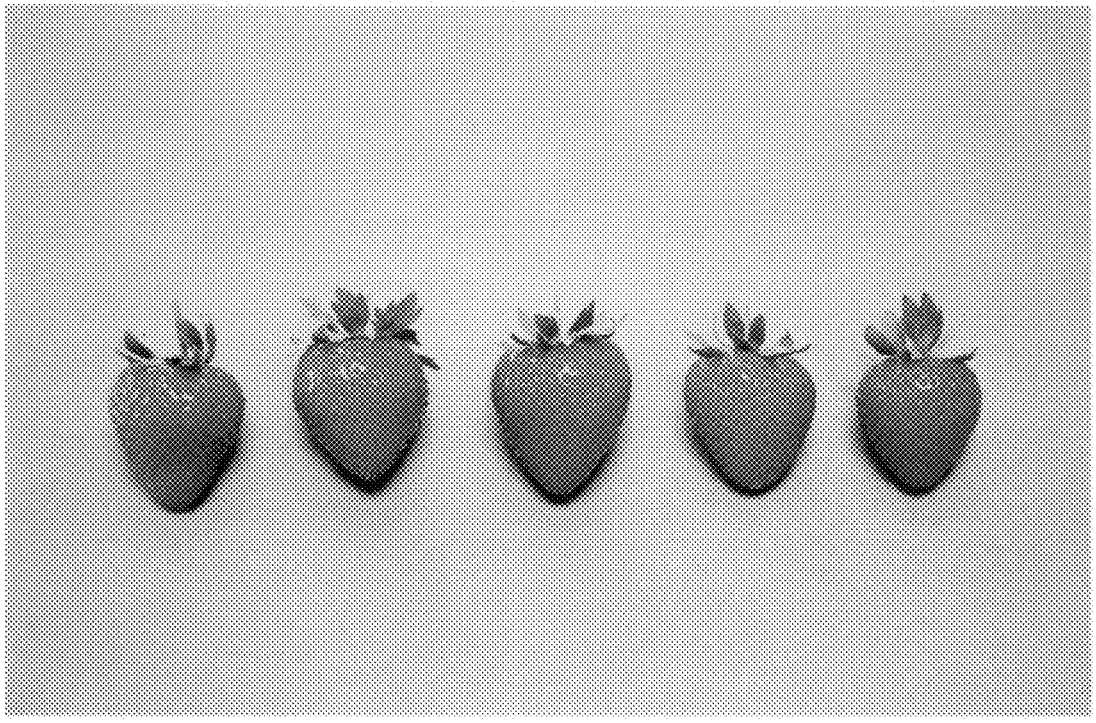
FIG. 4 shows the whole fruit.
Figure 5:
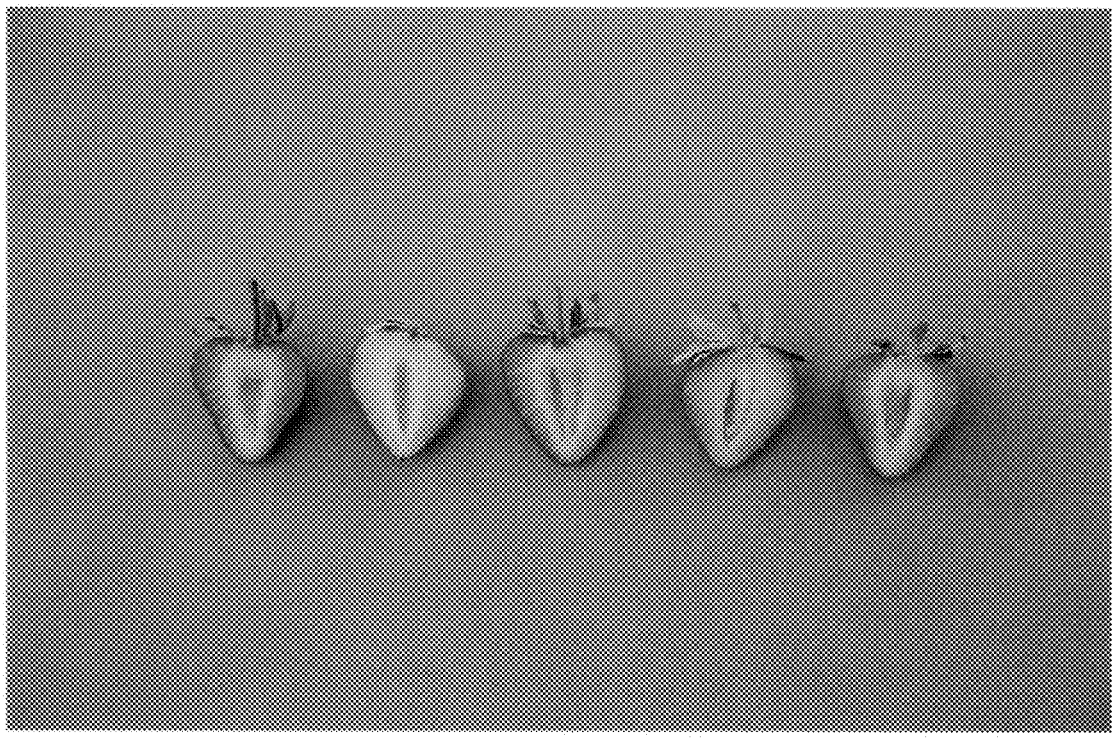
FIG. 5 shows the fruit in longitudinal cross-section.

The following description of 'DrisStrawFourteen' is based on observations taken in Monterey County, Calif. from 2005 to 2009. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFourteen' has not been observed under all possible environmental conditions. The botanical description of 'DrisStrawFourteen' was taken from 9-month-old plants and the botanical descriptions of the comparison varieties, 'San Juan' (U.S. Plant Pat. No. 12,899) and 'Driscoll Lanai' (U.S. Plant Pat. No. 15,145), were taken from 10-month-old plants and from 8-month-old plants, respectively. Color terminology follows The Royal Horticultural Society Colour Chart, London (RHS) (2001).

DETAILED BOTANICAL DESCRIPTION

Table 1 shows plant characteristics of the new variety compared with plant characteristics of the commercial varieties 'San Juan' and 'Driscoll Lanai'. Plant characteristics include plant height, diameter, number of crowns per plant, habit, the density of individual plants and the vigor.

TABLE 1

| Characteristic | 'DrisStrawFourteen' | 'San Juan' | 'Driscoll Lanai' |
|---|---|---|---|
| Plant height (cm) | 24.9 | 23.6 | 22.8 |
| Plant diameter (cm) | 39.6 | 44.2 | 40.1 |
| Number of crowns/ plant | 3 | 2 | 2 |
| Habit | Globose | Globose | Globose |
| Density of individual plant | Medium | Dense | Medium |
| Vigor | Medium | Strong | Medium |

Table 2 shows leaf characteristics of the new cultivar compared with leaf characteristics of 'San Juan' and 'Driscoll Lanai'. Leaf characteristics include terminal leaflet length and width in centimeters, length to width ratio, number of teeth per terminal leaflet, shape of teeth, color of upper side and underside of leaf, leaf shape in cross section, leaf blistering, leaf glossiness, number of leaflets, terminal leaflet margin, terminal leaflet length to width ratio, overall leaf shape and shape of leaf apex and base.

TABLE 2

| | 'DrisStrawFourteen' | 'San Juan' | 'Driscoll Lanai' |
|---|---|---|---|
| Leaf Characteristic | | | |
| Terminal leaflet length (cm) | 7.6 | 7.4 | 7.2 |
| Terminal leaflet width (cm) | 0.84 | 0.74 | 0.69 |
| Terminal leaflet length/width ratio | 0.9 | 1.0 | 1.0 |
| No. teeth/ terminal leaflet | 28 | 21 | 20 |
| Characteristic | | | |
| Shape of teeth | Obtuse | Rounded | Rounded |
| Color of upper surface of leaf | RHS 147A (Dark yellow-green) | RHS 139A (Dark green) | RHS 147A (Dark yellow-green) |
| Color of lower surface of leaf | RHS 148B (Medium yellow-green) | RHS 147B (Medium yellow-green) | RHS 148C (Medium yellow-green) |
| Leaf shape in cross section | Slightly concave | Slightly concave | Flat |
| Leaf blistering | Medium | Medium | Medium |
| Leaf glossiness | Medium | Medium | Medium |
| No. leaflets | 3 only | 3 only | 3 only |
| Terminal leaflet margin | Flat | Revolute to flat | Revolute to flat |
| Terminal leaflet length/width ratio | As long as broad | As long as broad | As long as broad |
| Terminal leaflet shape | Orbicular | Orbicular | Orbicular |
| Terminal leaflet base shape | Rounded | Rounded | Rounded |
| Terminal leaflet apex shape | Rounded | Rounded | Rounded |

Table 3 shows information about the petiole, the petiolule, the bract, and the stipule of the new cultivar compared to 'San Juan' and 'Driscoll Lanai'. This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 3

| Characteristic | 'DrisStrawFourteen' | 'San Juan' | 'Driscoll Lanai' |
|---|---|---|---|
| Petiole length (cm) | 13.8 | 16.3 | 14.4 |
| Petiole diameter (cm) | 0.333 | 0.314 | 0.280 |
| Petiole pubescence | Sparse | Medium | Medium |
| Petiole pose of hairs | Upwards to downwards | Outwards | Between upwards and outwards |
| Petiole color | RHS 144B (Medium yellow-green) | RHS 146B (Medium yellow-green) | RHS 144C (Medium yellow-green) |
| Petiolule color | RHS 144B (Medium yellow-green) | RHS 146C (Medium yellow-green) | RHS 144C (Medium yellow-green) |

TABLE 3-continued

| Characteristic | 'DrisStrawFourteen' | 'San Juan' | 'Driscoll Lanai' |
|---|---|---|---|
| Petiolule length (mm) | 7.21 | 8.63 | 12.26 |
| Petiolule diameter (cm) | 0.165 | 0.170 | 0.145 |
| Bract frequency | 1 | 1 | 0 |
| Stipule length (cm) | 3.8 | 3.3 | 3.3 |
| Stipule width (cm) | 0.694 | 0.929 | 0.897 |
| Stipule pubescence | Dense | Medium | Dense |
| Stipule anthocyanin coloration | RHS 145D (Light yellow-green) | RHS 149D (Light yellow-green) | RHS 149D (Light yellow-green) |

Table 4 shows stolon characteristics of the new cultivar compared to 'San Juan' and 'Driscoll Lanai'. These characteristics include the number of stolons, average number of daughter plants, the anthocyanin coloration of the stolons, the thickness of the stolons, and the pubescence of the stolons.

TABLE 4

| Characteristic | 'DrisStrawFourteen' | 'San Juan' | 'Driscoll Lanai' |
|---|---|---|---|
| Stolon number | Medium | Between medium and many | Many |
| Average number of daughter plants | 30+ | 57 | 67 |
| Stolon anthocyanin | RHS 60C (Dark red-purple) | RHS 59A (Dark red-purple) | RHS 60A (Dark red-purple) |
| Stolon thickness | Medium | Medium | Between medium and thick |
| Stolon pubescence | Medium | Medium | Dense |

Table 5 shows inflorescence characteristics of the new cultivar compared to 'San Juan' and 'Driscoll Lanai'. These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 5

| Characteristic | 'DrisStrawFourteen' | 'San Juan' | 'Driscoll Lanai' |
|---|---|---|---|
| Inflorescence position relative to foliage | Level with | Beneath | Level with |
| Time of flowering (50% of plants at first flower) | Between early and medium | Between early and medium | Between early and medium |
| Flower size | Medium | Medium | Medium |
| Flower diameter (cm) | 2.430 | 2.792 | 2.540 |
| Petal shape | Orbicular | Orbicular | Orbicular |
| Petal spacing | Overlapping | Overlapping | Overlapping |
| Petal apex shape | Rounded | Rounded | Rounded |

TABLE 5-continued

| Characteristic | 'DrisStrawFourteen' | 'San Juan' | 'Driscoll Lanai' |
|---|---|---|---|
| Petal margin | Entire | Entire | Entire |
| Petal base shape | Concave-convex | Concave-convex | Rounded |
| Petal length (cm) | 1.216 | 1.347 | 1.221 |
| Petal width (cm) | 1.149 | 1.469 | 1.285 |
| Petal length/width ratio | As long as broad | As long as broad | As long as broad |
| Petal length/width ratio | 1.1 | 0.9 | 1.0 |
| Typical and observed petal number | 6 | 6 | 7 |
| Petal color | RHS 155C (White) | RHS 155D (White) | RHS 155B (White) |
| Calyx diameter (cm) | 3.444 | 3.631 | 3.228 |
| Calyx diameter relative to corolla | Larger | Larger | Larger |
| Inner calyx diameter relative to outer | Same size | Same size | Same size |
| Sepal shape | Oval | Oval | Oval |
| Sepal apex shape | Convex | Convex | Convex |
| Sepal margin | Entire | Entire | Entire |
| Sepal length (cm) | 1.369 | 1.461 | 1.150 |
| Sepal width (cm) | 0.681 | 0.767 | 0.461 |
| Typical and observed sepal number | 13 | 13 | 13 |
| Receptacle color | RHS 2A (Medium yellow) | RHS 151A (Medium yellow-green) | RHS N144B (Medium yellow-green) |
| Anther color | RHS 152B (Medium yellow-green) | RHS 178A (Dark greyed-red) | RHS 163A (Medium greyed-orange) |

Table 6 shows fruit characteristics of the new cultivar compared to 'San Juan' and 'Driscoll Lanai'. These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 6

| Characteristic | 'DrisStrawFourteen' | 'San Juan' | 'Driscoll Lanai' |
|---|---|---|---|
| Fruiting truss length (cm) | 18.8 | 22.8 | 17.2 |
| Fruiting truss length (general) | Medium | Between medium and long | Medium |
| Fruiting truss diameter (cm) at base of truss | 0.429 | 0.391 | 0.327 |
| Number of berries per fruiting truss | 4 | 4 | 4 |
| Fruiting truss attitude | Prostrate | Prostrate | Prostrate |
| Fruiting truss color at base of truss | RHS 144A (Medium yellow-green) | RHS 144A (Medium yellow-green) | RHS 144A (Medium yellow-green) |
| Fruit length (cm) | 4.149 | 4.349 | 3.752 |
| Fruit width (cm) | 3.840 | 3.784 | 3.683 |

TABLE 6-continued

| Characteristic | 'DrisStrawFourteen' | 'San Juan' | 'Driscoll Lanai' |
|---|---|---|---|
| Fruit length/width ratio | 1.1 | 1.1 | 1.0 |
| Fruit hollow length (cm) | 2.139 | 1.837 | 1.222 |
| Fruit hollow width (cm) | 0.716 | 0.538 | 0.424 |
| Fruit hollow length/width ratio | 3.0 | 3.4 | 2.9 |
| Fruit weight (g) | 29.1 | 25.4 | 24.9 |
| Fruit ratio of length/maximum width | As long as broad | As long as broad | As long as broad |
| Relative fruit size | Medium | Medium | Medium |
| Predominant fruit shape | Conical | Conical | Conical and almost cylindrical |
| Difference in shape between primary and secondary fruits | Slight | Slight | Slight |
| Band without achenes | Absent or very narrow | Broad | Narrow |
| Unevenness of fruit surface | Weak | Medium | Weak |
| Fruit skin color | RHS 46B (Dark red) | RHS 46A (Dark red) | RHS 46A (Dark red) |
| Evenness of fruit color | Even | Slightly uneven | Even |
| Fruit glossiness | Medium | Medium | Medium |
| Insertion of achenes | Below surface to above surface | Level with surface | Above surface |
| Achene coloration (sunward side of berry) | RHS 185A (Dark greyed-purple) | RHS 183C (Dark greyed-purple) | RHS 176A (Dark greyed-orange) |
| Achene coloration (shaded side of berry) | RHS N144B (Medium yellow-green) | RHS 152C (Medium yellow-green) | RHS 152C (Medium yellow-green) |
| Achenes per berry | 340.6 | 273.4 | 294.5 |

Table 7 shows fruit characteristics of the new cultivar compared to 'San Juan' and 'Driscoll Lanai'. These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 7

| Characteristic | 'DrisStrawFourteen' | 'San Juan' | 'Driscoll Lanai' |
|---|---|---|---|
| Harvest interval | Late March to early November | Late March to early November | Late March to early November |
| Harvest maturity | Late | Between early and mid-season | Between early and mid-season |
| Insertion of calyx | Level | Set above fruit | Level |
| Pose of calyx segments | Reflexed | Reflexed | Reflexed |
| Size of calyx in relation to fruit | From same size to larger | Same size | From same size to larger |
| Adherence of calyx | Strong | Strong | Medium |
| Firmness of flesh | Firm | Medium | Medium |
| Color of the flesh | RHS 155D (White) and RHS 43B (Medium red) | RHS 155B (White) and RHS 43A (Medium red) | RHS 155C (White) and RHS 46A (Dark red) |

TABLE 7-continued

| Characteristic | 'DrisStrawFourteen' | 'San Juan' | 'Driscoll Lanai' |
|---|---|---|---|
| Evenness of flesh color | Slightly uneven | Slightly uneven | Slightly uneven |
| Distribution of flesh color | Marginal and central | Marginal and central | Marginal and central |
| Hollow center | Large | Small | Small |
| Sweetness | Medium | Medium | Medium |
| Acidity | Medium | Medium | Medium |
| Texture when tasted | Medium | Medium | Medium |
| Type of bearing | Partially everbearing | Partially everbearing | Partially everbearing |
| Grams of fruit/ plant | 1,463 | 1,303 | 1,699 |

Table 8 shows pest, stress and disease characteristics of the new cultivar compared to 'San Juan' and 'Driscoll Lanai'.

TABLE 8

| Pest, Stress, or Disease | 'DrisStrawFourteen' | 'San Juan' | 'Driscoll Lanai' |
|---|---|---|---|
| *Botrytis* fruit rot | Moderately resistant | Susceptible | Susceptible |
| Powdery mildew | Between resistant and moderately resistant | Susceptible | Susceptible |
| *Verticillium* wilt | Moderately resistant | Susceptible | Moderately susceptible |
| Rain | Between resistant and moderately resistant | Between resistant and moderately resistant | Moderately resistant |

COMPARISON WITH PARENTAL AND COMMERCIAL CULTIVARS

When 'DrisStrawFourteen' is compared to the proprietary female parent '159K312' (unpatented), 'DrisStrawFourteen' has larger fruit and better organic performance than does '159K312 ' .

When 'DrisStrawFourteen' is compared to the proprietary male parent '128K296' (unpatented), 'DrisStrawFourteen' has larger fruit and better organic performance than does '128K296'.

When 'DrisStrawFourteen' is compared to the commercial variety 'San Juan', 'DrisStrawFourteen' has softer but more fruit in the second half of the season than does 'San Juan'.

Table 9 shows selected plant characteristics of the new variety compared with plant characteristics of 'San Juan' (U.S. Plant Pat. No. 12,899) and 'Driscoll Lanai' (U.S. Plant Pat. No. 15,145). Plant characteristics include terminal leaflet margin profile, insertion of achenes, and fruit production.

TABLE 9

| Characteristic | 'DrisStrawFourteen' | 'San Juan' | 'Driscoll Lanai' |
|---|---|---|---|
| Terminal leaflet margin profile | Flat | Revolute to flat | Revolute to flat |
| Insertion of achenes | Below surface to above surface | Level with surface | Above surface |
| Fruit production, grams/plant | 1,463 | 1,303 | 1,699 |

We claim:

1. A new and distinct cultivar of strawberry plant as described and shown herein.

* * * * *